United States Patent
Maier

(10) Patent No.: US 8,456,649 B2
(45) Date of Patent: Jun. 4, 2013

(54) RETRO-REFLECTOR FOR IMAGE-GUIDED OPERATION SYSTEMS

(75) Inventor: Christian Maier, München (DE)

(73) Assignee: Brainlab AG, Feldkirchen (DE)

( * ) Notice: Subject to any disclaimer, the term of this patent is extended or adjusted under 35 U.S.C. 154(b) by 442 days.

(21) Appl. No.: 12/553,115

(22) Filed: Sep. 3, 2009

(65) Prior Publication Data
US 2010/0053639 A1    Mar. 4, 2010

Related U.S. Application Data

(60) Provisional application No. 61/115,716, filed on Nov. 18, 2008.

(30) Foreign Application Priority Data

Sep. 3, 2008   (EP) .................................... 08163608

(51) Int. Cl.
- *G01B 11/14* (2006.01)
- *G02B 5/124* (2006.01)
- *G02B 5/122* (2006.01)

(52) U.S. Cl.
USPC ........................ 356/620; 359/514; 359/529

(58) Field of Classification Search
USPC ................. 359/513–514, 529–533; 356/620
See application file for complete search history.

(56) References Cited

U.S. PATENT DOCUMENTS

| | | | |
|---|---|---|---|
| 3,684,348 A * | 8/1972 | Rowland | 359/530 |
| 3,922,065 A * | 11/1975 | Schultz | 359/514 |
| 3,924,929 A * | 12/1975 | Holmen et al. | 359/514 |
| 3,977,765 A | 8/1976 | Lipkins | |
| 4,066,331 A * | 1/1978 | Lindner | 359/514 |
| 5,589,981 A | 12/1996 | Kasser et al. | |
| 5,834,759 A * | 11/1998 | Glossop | 250/203.1 |
| 6,185,055 B1 * | 2/2001 | Feist | 359/831 |
| 7,179,406 B1 * | 2/2007 | Attar | 264/1.9 |
| 2001/0033906 A1 * | 10/2001 | Smith et al. | 428/40.1 |
| 2003/0227683 A1 * | 12/2003 | Sewall et al. | 359/530 |
| 2006/0109548 A1 * | 5/2006 | Goto | 359/449 |
| 2006/0241388 A1 | 10/2006 | Lavallee | |
| 2007/0035835 A1 | 2/2007 | Hadden | |
| 2007/0153297 A1 * | 7/2007 | Lau | 356/620 |
| 2008/0131115 A1 | 6/2008 | Habberstad et al. | |

FOREIGN PATENT DOCUMENTS

| | | |
|---|---|---|
| EP | 1 774 922 | 4/2007 |
| EP | 1 908 406 | 4/2008 |
| FR | 2 691 129 | 11/1993 |
| WO | 99/58065 | 11/1999 |

\* cited by examiner

*Primary Examiner* — Stephone Allen
*Assistant Examiner* — Kimberly N Kakalec
(74) *Attorney, Agent, or Firm* — Renner, Otto, Boisselle & Sklar, LLP

(57) ABSTRACT

A retro-reflector for image-guided operation systems, comprising eight cube corners, wherein the tips of the cube corners are adjacent to each other and each cube corner is formed from three reflective faces, comprising a protection against contamination which prevents dirt from being deposited in the cube corners.

8 Claims, 5 Drawing Sheets

RETRO-REFLECTOR FOR IMAGE-GUIDED OPERATION SYSTEMS

RELATED APPLICATION DATA

This application claims the priority of U.S. Provisional Application No. 61/115,716, filed on Nov. 18, 2008, which is hereby incorporated in its entirety by reference.

FIELD OF THE INVENTION

The present invention relates to a retro-reflector for image-guided operation systems, a manufacturing method for a retro-reflector, an image-guided operation system and the use of a retro-reflector in an image-guided operation system.

BACKGROUND OF THE INVENTION

In image-guided operation systems, objects—for example, medical instruments or bones—are provided with marker devices in order to be able to ascertain the location, i.e. the position and/or alignment, of the object. The marker devices are usually one or more diffusely reflective spheres which reflect the light emitted from a light source. The reflected light is detected by a sensor, for example a 3D camera. The centre point of each reflection is ascertained in a computational unit and regarded as the centre point of a sphere for the subsequent calculation of the location. One problem occurs when a sphere is partially covered and the sensor can therefore only partially detect the reflection. The centre point of the reflection is also assumed as the centre point of the sphere in this case, but does not correspond to the actual centre point of the sphere. This usually leads to an error in calculating the location of the object.

This is avoided by using a retro-reflector in the marker device. A retro-reflector reflects back incident radiation, for example light, parallel to its direction of incidence. This occurs due to multiple reflection in the retro-reflector, wherein each incident beam experiences a parallel shift. Because of this parallel shift, the radiation path as a whole is interrupted as soon as the retro-reflector is covered over too great an area. Accordingly, the retro-reflector can only be detected by the sensor when it is sufficiently visible and can therefore be correctly localized.

It is often necessary in an image-guided operation system for the retro-reflector to possess retro-reflective properties all around, i.e. in all spatial directions. Such a retro-reflector is for example disclosed in the published patent application specification US 2008/0131115 A1. The retro-reflector shown in this document consists of eight cube corners, wherein the tips of the cube corners are adjacent to each other and each cube corner is formed from three reflective faces. The retro-reflector serves to detect a sound field, by modulating the retro-reflective radiation using a membrane situated in one of the reflective faces.

SUMMARY OF THE INVENTION

It is object of the present invention to provide a retro-reflector which is suitable for image-guided operation systems and is designed to be robust.

This object is solved by a retro-reflector for image-guided operation systems, comprising eight cube corners, wherein the tips of the cube corners are adjacent to each other and each cube corner is formed from three reflective faces, comprising a protection against contamination which prevents dirt from being deposited in the cube corners. Manufacturing methods for such a retro-reflector are specified by a manufacturing method in which eight cube corners—each consisting of three reflective faces—are arranged such that their tips are adjacent to each other, wherein the cube corners are provided with a protection against contamination, and by a manufacturing method in which eight transparent partial bodies are produced, side faces of the partial bodies are coated with a reflective material, and the coated partial bodies are assembled to form the retro-reflector. An image-guided operation system comprising a retro-reflector in accordance with the invention, and the use of a retro-reflector consisting of eight cube corners in an image-guided operation system, are also specified.

The retro-reflector for image-guided operation systems comprises eight cube corners and in particular only eight cube corners exactly, wherein the tips of the cube corners are adjacent to each other and each cube corner is formed from three reflective faces. Accordingly, the tips of the cube corners contact each other in a centre point of the retro-reflector. The centre point of the retro-reflector is the point in which the planes in which the reflective faces of the retro-reflector lie intersect each other. The tip of a cube corner is the point at which the three reflective faces converge.

In accordance with the invention, the retro-reflector comprises a protection against contamination which prevents dirt from being deposited in the cube corners. This allows the retro-reflector to be easily cleaned, in particular disinfected, after use—for example, after an operation. The protection against contamination is in particular designed to prevent (adhering) contact between dirt, in particular dust or liquid, and the reflective faces.

In one embodiment of the invention, the protection against contamination is a dirt-repellent coating on the reflective faces, in particular a nano-coating. In another embodiment of the invention, the protection against contamination is a surface which is positioned in front of the tips of the cube corners, i.e. said surface exhibits a distance from the tip of a cube corner which is for example greater than 1 mm, 2 mm, 5 mm or 1 cm and/or greater than 0.1 or 0.5 or 1 times the edge length of the edge of a reflective face, which extends out from the tip of the cube corner. The surface positioned in front is optionally coated with a dirt-repellent coating, for example a nano-coating.

In one embodiment of the invention, the protection against contamination comprises a transparent shell which surrounds the cube corners and in particular exhibits a smooth surface. Accordingly, the cube corners are completely enveloped by the transparent shell. The shell is for example shaped as a spherical shell or a hollow cuboid, in particular a hollow cube. Due to the effect of the shell on the radiation path, the shell should be designed to be as thin as possible, for example thinner than 2 mm, thinner than 1 mm, or thinner than 0.5 mm, and should exhibit a refraction index which is as near as possible to the refraction index of air, for example less than 2, less than 1.8 or less than 1.5. The refraction index is for example specified for a wavelength of 589 nm, or for infrared radiation at room temperature.

It may be noted that the terms "reflective" and "transparent" within the framework of this document relate to radiation of a wavelength which is to be reflected by the retro-reflector, for example visible light or in particular infrared radiation.

In one alternative embodiment of the invention, the protection against contamination comprises a filling of the cube corners comprising transparent material. This also prevents contaminants from being deposited in the edges and in particular the tip of the cube corners. The filling is preferably embodied such that it produces a smooth surface for the retro-reflector. Such a surface is for example that of a sphere or cuboid, in particular a cube.

The reflective faces of the cube corners are for example formed by reflectively coated walls. One wall can also be reflectively coated on both sides and thus form two reflective faces of two adjacent cube corners. In another embodiment of the invention, the reflective faces are formed by walls made of reflective material. In this case, too, one wall can form two reflective faces of two adjacent cube corners.

In the case of a filling of the cube corners comprising transparent material, it is in particular possible for the reflective faces of the cube corners to be formed by partially coating the filling. The filling is for example cast with the aid of a mould, such that an octant of a sphere, an equilateral pyramid with a triangular base or a cuboid is created. The three even faces of the octant, the three side faces of the pyramid or three side faces of the cuboid are then provided with a reflective coating and then assembled to form the retro-reflector, wherein each two coated faces contact each other. Alternatively, only one of the two faces which contact each other when assembled is provided with a reflective coating.

The retro-reflector preferably comprises a supporting rod by means of which the retro-reflector can be fastened to an object. In one embodiment of the invention, the centre axis of the supporting rod matches the line of intersection between two reflective faces of one of the cube corners. In this case, the supporting rod runs or ends in an edge of one or more adjacent cube corners. The supporting rod thus at least partially forms the extension of an edge formed by two reflective faces of a cube corner. This arrangement has the advantage that the supporting rod does not impair the reflection properties of any of the cube corners.

In one alternative embodiment, the supporting rod is arranged centrally in one of the cube corners and fixedly connected to the tip of said cube corner. "Arranged centrally" means that a point on the centre axis of the supporting rod exhibits the same distance from each of the three reflective faces of the cube corner. In other words, the projection of the centre axis of the supporting rod into one of the reflective faces forms the angle bisector between the two other reflective faces. This arrangement does obstruct retro-reflection in the corresponding cube corner, but said cube corner faces the marked object and is thus covered by said object when the location is being detected anyway.

In a manufacturing method for a retro-reflector, eight cube corners—each consisting of three reflective faces—are firstly arranged such that their tips are adjacent to each other. The cube corners are then provided with a protection against contamination. The reflective faces are for example formed from a substrate material which is provided with a reflective layer, or the reflective faces are formed from walls which consist of reflective material.

In one embodiment of the manufacturing method, the protection against contamination is produced by filling the cube corners with a transparent material, wherein the cube corners are for example effused. Various surface shapes for the retro-reflector can be produced by configuring the filling.

In an alternative embodiment of the manufacturing method, the protection against contamination is produced by enveloping the cube corners with a transparent shell. The transparent shell is produced for example by means of injection molding. One way is to produce two half-shells which are placed around the cube corners and connected to each other, wherein the connection line between the two half-shells preferably coincides with the rims of reflective faces. The connection line is thus not situated in the radiation path of incident or reflected light.

In another alternative manufacturing method, eight partial bodies are produced from transparent material. Side faces of the partial bodies are then coated with a reflective material, and the coated partial bodies are assembled to form the retro-reflector. The side faces can be coated using any suitable coating technique, for example depositing, spraying or bonding. Either all three side faces of each partial body which contact a side face of another partial body in the assembled retro-reflector are coated, or only one of two mutually contacting side faces of adjacent partial bodies is coated.

The eight partial bodies are preferably produced from a transparent solid body by three cuts, i.e. the solid body is cut into eights, wherein the three cuts are preferably perpendicular to each other. If material is lost when making the cuts, for example in a machining method, the layers are preferably designed to be thick enough that they compensate for the removed material of the solid body. Accordingly, the solid body—once assembled—has exactly its original form again.

The invention also relates to an image-guided operation system comprising a light source, at least one retro-reflector as described above for reflecting the light of the light source, at least one detector for detecting the reflected light and a computational unit for calculating the position of the retro-reflector from the output signal of the detector. The detector is for example a camera, in particular a 3D camera. The light source is preferably situated in the immediate vicinity of the detector. The location of the object marked with the retro-reflector follows from the location of the retro-reflector.

The invention also relates to the use of a retro-reflector consisting of eight cube corners, wherein the tips of the cube corners are adjacent to each other and each cube corner is formed from three reflective faces, in an image-guided operation system.

BRIEF DESCRIPTION OF THE DRAWINGS

The present invention shall be illustrated in more detail on the basis of example embodiments.

DETAILED DESCRIPTION

Figure 1:
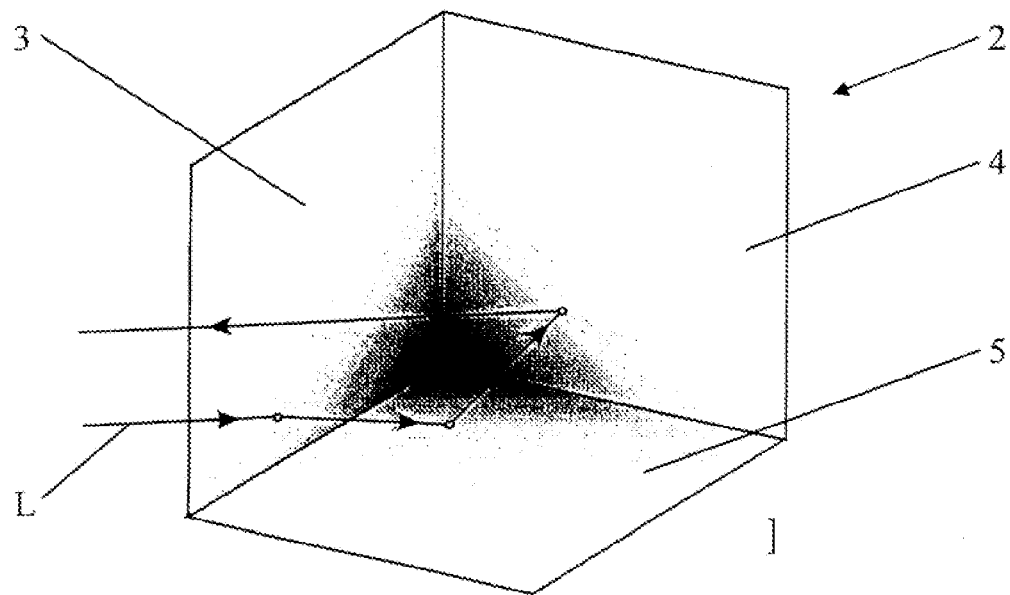
FIG. 1 shows a cube corner.

FIG. 1 schematically shows an individual cube corner 2, which is also referred to as a three-fold mirror. The cube corner 2 consists of three faces 3, 4 and 5 which are perpendicular to each other, respectively. The faces 3, 4 and 5 consist of walls which are provided with a reflective coating, for example a coating made of silver, aluminum, copper, gold or mixtures of these metals. The reflective coating can be provided with a dirt-repellent nano-coating. The exemplary beam of light L which hits the cube corner 2 is firstly reflected on the face 3, then on the face 5 and finally on the face 4, such that it is ultimately reflected back by the cube corner 2 parallel to the direction of incidence, at an offset.

Figure 2:
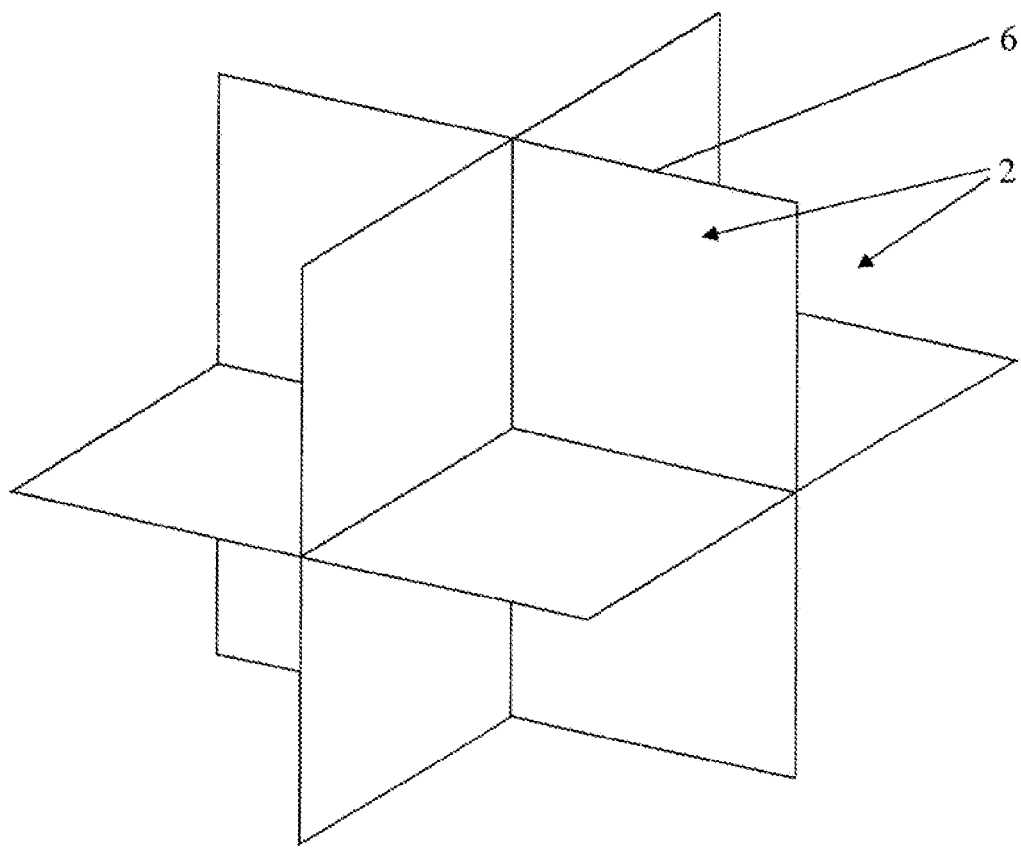
FIG. 2 shows a first arrangement of eight cube corners.

FIG. 2 shows a first arrangement of eight cube corners 2, the tips of which are adjacent to each other in the centre point of the arrangement. The reflective faces of the cube corners 2 are formed by reflectively coated walls, wherein each wall is coated on both sides and thus forms two reflective faces for two adjacent cube corners 2. The reflective faces and therefore the walls of each cube corner 2 are respectively perpendicular to each other, such that each four of the total of twelve walls lie in a common plane. Using the arrangement shown in FIG. 2, a beam of light entering from any spatial direction can be reflected back parallel to its direction of incidence.

The reflective faces are each shaped as a rectangle, in particular a square, such that the edges 6 of the arrangement of eight cube corners 2 also each exhibit the shape of a rectangle and/or square. The edges 6 of the arrangement are composed of the edges of the reflective faces which are not adjacent to other reflective faces. Each of the edges 6 consists of the edges of the reflective faces which lie in the same plane.

Figure 3:
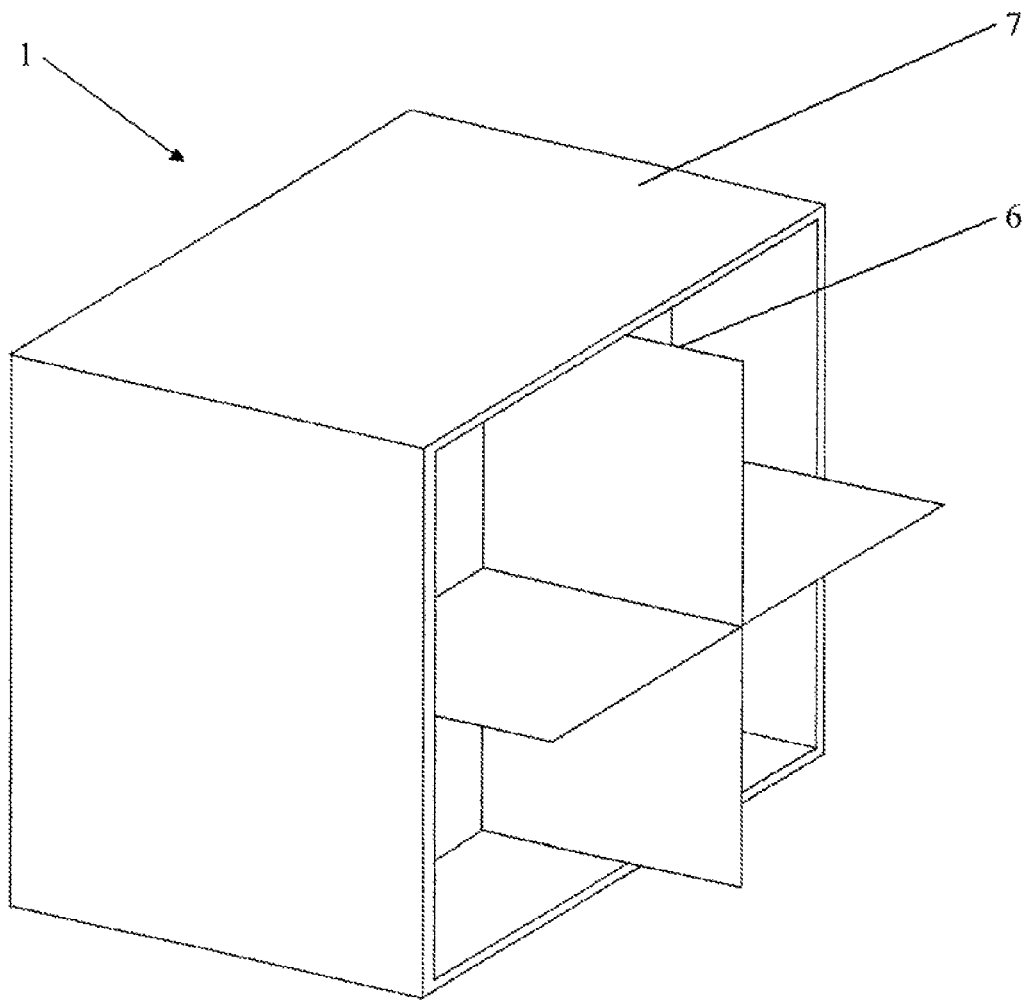
FIG. 3 shows the arrangement from FIG. 2, surrounded by a shell.

FIG. 3 shows a retro-reflector 1 in which the arrangement of eight cube corners 2 from FIG. 2 has been surrounded by a transparent shell 7 in the form of a hollow cuboid, for example a hollow cube. The shell 7 is shown sectioned in FIG. 3, wherein the size of the cuboid and/or cube is selected such that the edges 6 of the walls of the cube corners 2 abut the interior surface of the cuboid and/or cube. Preferably, the edges 6 are fixedly connected, for example bonded, to the interior surface of the shell 7, which increases the stability of the cube corners 2.

Figure 4:
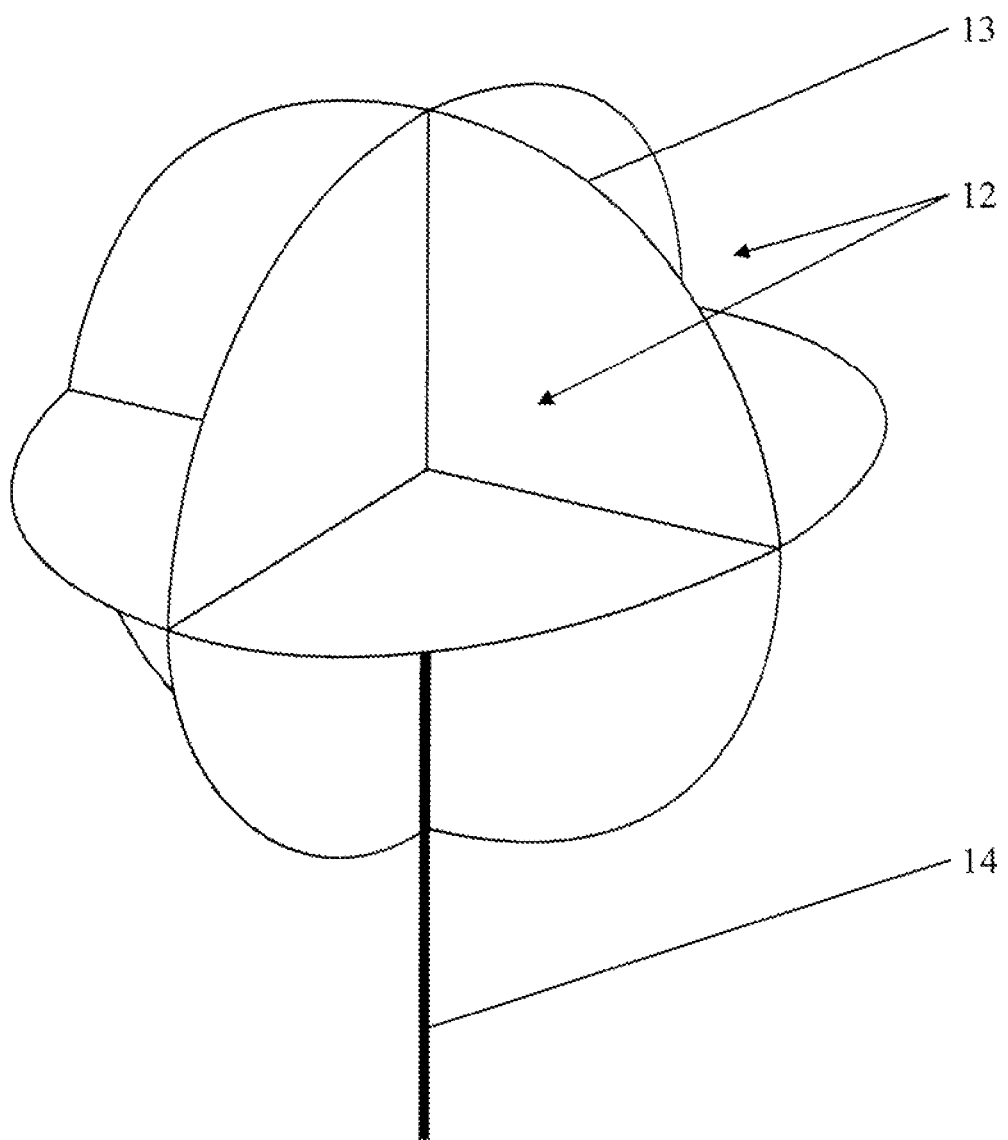
FIG. 4 shows a second arrangement of eight cube corners.

FIG. 4 shows a second arrangement of eight cube corners 2, wherein the reflective faces of the cube corners 2 are not rectangles but rather circular sectors. Each sector corresponds to a quarter of a circular disc. The reflective faces are respectively connected to each other at their radial edges and are perpendicular to each other. This results in an arrangement of eight cube corners 2, wherein the three edges 13 of the arrangement exhibit the shape of full circles. The edges 13 of the arrangement are composed of the edges of the reflective faces which are not adjacent to other reflective faces. Each of the edges 13 consists of the edges of the reflective faces which lie in the same plane. The arrangement of eight cube corners forms the core of a retro-reflector 1.

A supporting rod 14 is also provided which extends out from the centre point of the arrangement of the eight cube corners 12, along the line of intersection between two side faces of one of the cube corners 12. The supporting rod 14 thus lies exactly in the edge at which two walls of a cube corner 12 contact each other. The reflection properties of this cube corner are not therefore impaired. The supporting rod 14 serves to fasten the retro-reflector 11 to an object, the location of which is to be determined.

Figure 5:
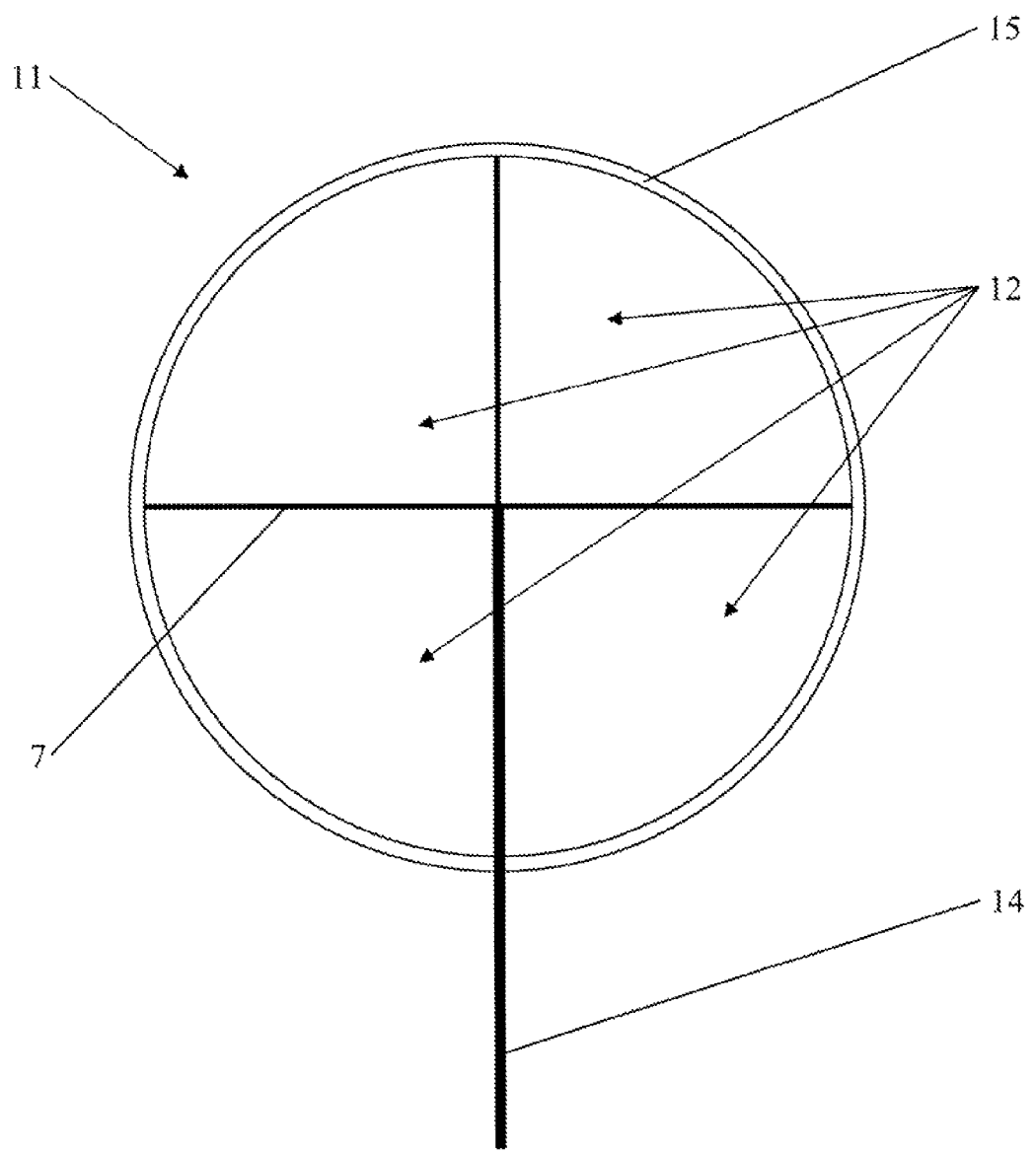
FIG. 5 shows a sectional representation of a retro-reflector.

FIG. 5 shows the retro-reflector 11 in a partially sectioned lateral view, wherein the arrangement of eight sphere corners 12 from FIG. 4 is enveloped by a spherical shell 15. The spherical shell 15 consists of two half-shells. When manufacturing the retro-reflector 11, the arrangement of eight cube corners 12 is inserted into the first half-shell, then the second half-shell is placed on top and connected to the first half-shell, for example by bonding, wherein the connection line between the two half-shells preferably directly abuts one of the three circular edges 13. The connection area between the two half-shells does not therefore form a disruption in the radiation path.

The exterior diameter of the retro-reflector 11, including the interval rims, is preferably between 1 cm and 2 cm. The wall thickness of the walls of the cube corners 12 and spherical shell 15 is preferably less than a twentieth of the diameter of the retro-reflector 11.

As an alternative to encapsulating the arrangements of eight cube corners 2 or 12, respectively, in a hollow cuboid and/or cube 7 or a spherical shell 15, the cube corners 1, 12 are filled with a transparent material. In the case of the arrangement of FIG. 2, the filling is designed such that the exterior surface of the retro-reflector 1 exhibits the shape of a cuboid and/or cube. In the case of the arrangement of the cube corners in FIG. 4, the filling is embodied such that the retro-reflector 11 exhibits the exterior shape of a sphere.

Figure 6:
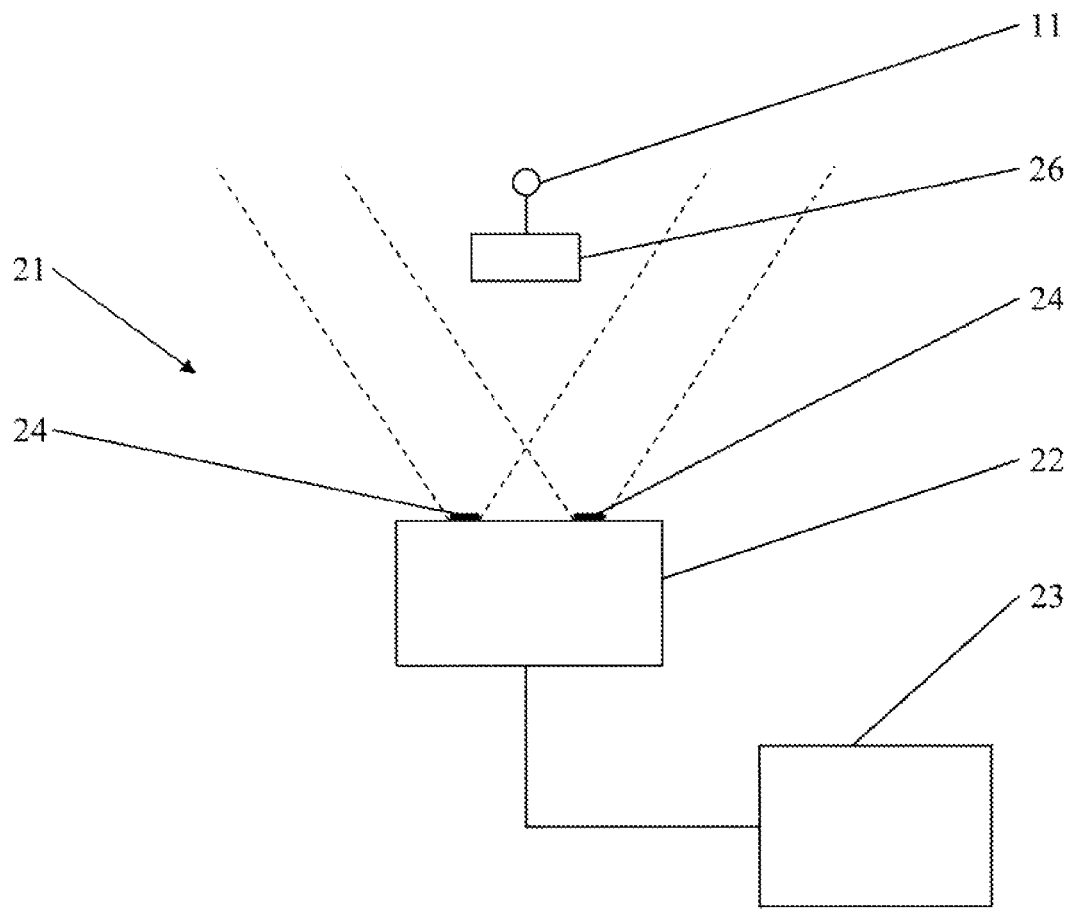
FIG. 6 shows an image-controlled operation system.

FIG. 6 schematically shows an image-guided operation system 21 comprising a 3D camera 22 and a computational unit 23. The 3D camera comprises two image sensors 24 which each record a two-dimensional image. The detection ranges of the image sensors 24 are indicated by broken lines.

The image-guided operation system 21 is configured to determine the location of an object 26. To this end, the object 26 is fixedly connected to a retro-reflector 11. The fixed connection between the object 26 and the retro-reflector 11 means that their locations relative to each other have a fixed relationship. If the location of the retro-reflector 11 is known, the location of the object 26 can be directly determined from this.

Figure 7:
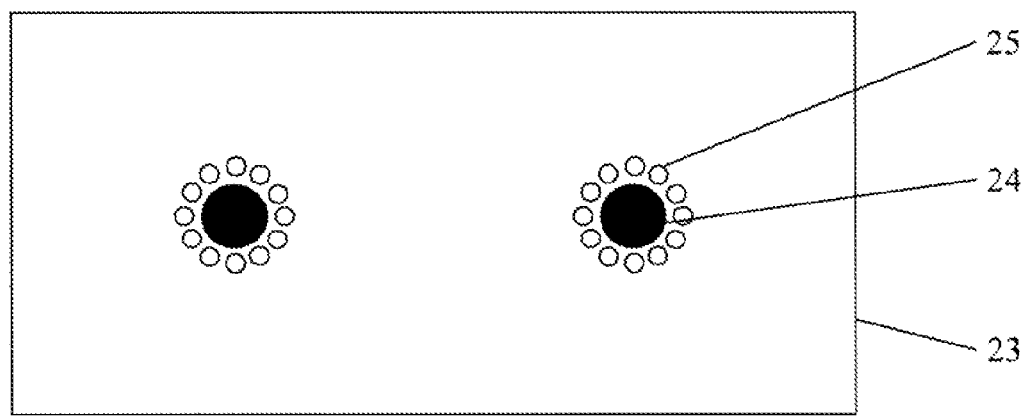
FIG. 7 shows a front view of a 3D camera.

As can be seen from the schematic front view of the 3D camera in FIG. 7, each of the image sensors 24 is surrounded by a ring of light-emitting diodes 25, wherein the light-emitting diodes 25 preferably emit light in the infrared range. The emitted light hits the retro-reflector 11 and is reflected back onto the two image sensors 24. The output signals of the image sensors 24 are transmitted to the computational unit 23, where they are evaluated. Since the two image sensors 24 detect the retro-reflector 11 from different positions, the spatial position of the retro-reflector 11 and therefore the spatial position of the object can be determined. If a number of retro-reflectors 11 are arranged on the object 26, it is then possible to determine not only the position but also the alignment of the object 26 from the detected positions of the retro-reflectors 11. At least three retro-reflectors 11 are preferably combined to form a marker device, and connected to the object 26.

Computer program elements of the invention may be embodied in hardware and/or software (including firmware, resident software, micro-code, etc.). The computer program elements of the invention may take the form of a computer program product which may be embodied by a computer-usable or computer-readable storage medium comprising computer-usable or computer-readable program instructions, "code" or a "computer program" embodied in said medium for use by or in connection with the instruction executing system. Within the context of this application, a computer-usable or computer-readable medium may be any medium which can contain, store, communicate, propagate or transport the program for use by or in connection with the instruction executing system, apparatus or device. The computer-usable or computer-readable medium may for example be, but is not limited to, an electronic, magnetic, optical, electro-magnetic, infrared or semiconductor system, apparatus, device or medium of propagation, such as for example the Internet. The computer-usable or computer-readable medium could even for example be paper or another suitable medium on which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiment(s).

Although the invention has been shown and described with respect to one or more particular preferred embodiments, it is clear that equivalent amendments or modifications will occur to the person skilled in the art when reading and interpreting the text and enclosed drawing(s) of this specification. In particular with regard to the various functions performed by the elements (components, assemblies, devices, compositions, etc.) described above, the terms used to describe such elements (including any reference to a "means") are intended, unless expressly indicated otherwise, to correspond to any element which performs the specified function of the element described, i.e. which is functionally equivalent to it, even if it is not structurally equivalent to the disclosed structure which performs the function in the example embodiment(s) illustrated here. Moreover, while a particular feature of the invention may have been described above with respect to only one or some of the embodiments illustrated, such a feature may also be combined with one or more other features of the other embodiments, in any way such as may be desirable or advantageous for any given application of the invention.

What is claimed is:

1. A system for tracking an object in three-dimensional space, comprising:
   a marker device including
   i) eight cube corners each formed from three reflective faces, the intersection of the three reflective faces defining a tip of a respective cube corner, wherein the tips of the eight cube corners are adjacent to a common point, and
   ii) a protection device configured to prevent contaminants from being deposited in the cube corners; and
   a medical tracking system including
   i) a plurality of sensors spaced apart from one another and configured to detect light reflected by the marker device, and
   ii) a computational unit operatively coupled to the plurality of sensors, the computational unit configured to determine a position of the marker device in three-dimensional space based on the light detected by the plurality of sensors.

2. The system according to claim 1, wherein the protection device comprises a transparent shell which surrounds the cube corners.

3. The system according to claim 1, wherein the protection device comprises a transparent material arranged within each cube corner.

4. The system according to claim 3, wherein the reflective faces are formed by partially coating the transparent material.

5. The system according to claim 1, wherein the reflective faces are formed by coated walls or by walls made of reflective material.

6. The system according to claim 1, comprising a supporting rod, the centre axis of which matches the line of intersection between two reflective faces of one of the cube corners.

7. The system according to claim 1, comprising a supporting rod which is arranged centrally in one of the cube corners and fixedly connected to the tip of the one cube corner.

8. A method of tracking an object in three-dimensional space via an image-guided navigation system, comprising:
   using a medical tracking system that includes a plurality of sensors spaced apart from one another to detect light reflected by a retro-reflector that comprises eight cube corners each formed from three reflective faces, the intersection of the three reflective faces defining a tip of a respective cube corner, wherein the tips of the eight cube corners are adjacent to a common point; and
   determining a location of the object in three-dimensional space based on the detected light.

* * * * *